US008932322B2

(12) United States Patent
Reynolds et al.

(10) Patent No.: US 8,932,322 B2
(45) Date of Patent: Jan. 13, 2015

(54) NEUROMUSCULAR RELEASE THERAPY DEVICE, SYSTEM AND METHODS

(75) Inventors: Jonathan F. Reynolds, Eagan, MN (US); Alexander G. Barr, Burnsville, MN (US); James M. Poplett, Plymouth, MN (US); Raoul G. Antelme, Leysin (CH)

(73) Assignee: Hogsback Inc., Eagan, MN (US)

( * ) Notice: Subject to any disclaimer, the term of this patent is extended or adjusted under 35 U.S.C. 154(b) by 433 days.

(21) Appl. No.: 13/226,241

(22) Filed: Sep. 6, 2011

(65) Prior Publication Data

US 2012/0059405 A1 Mar. 8, 2012

Related U.S. Application Data

(60) Provisional application No. 61/379,924, filed on Sep. 3, 2010.

(51) Int. Cl.

| | |
|---|---|
| ***A61B 17/00*** | (2006.01) |
| ***A61H 39/04*** | (2006.01) |
| ***A61H 23/02*** | (2006.01) |
| *A61H 11/00* | (2006.01) |

(52) U.S. Cl.

CPC ................ *A61H 39/04* (2013.01); *A61H 23/02* (2013.01); *A61H 11/00* (2013.01); *A61H 2201/0107* (2013.01); *A61H 2201/0157* (2013.01); *A61H 2201/0161* (2013.01); *A61H 221/0207* (2013.01); *A61H 2201/0214* (2013.01); *A61H 2201/1284* (2013.01); *A61H 2201/1661* (2013.01); *A61H 2201/168* (2013.01); *A61H 2201/1695* (2013.01); *A61H 2205/081* (2013.01)

USPC .......................................... 606/204; 606/201

(58) Field of Classification Search

CPC .... A61B 17/12; A61B 17/1325; A61H 39/04; A61H 7/001

USPC .......... 606/204, 201; 601/134, 135, 136, 137, 601/23, 27, 28; D24/200, 214

See application file for complete search history.

(56) References Cited

U.S. PATENT DOCUMENTS

| | | | | |
|---|---|---|---|---|
| 4,126,129 | A | 11/1978 | Rainbow | |
| 4,210,134 | A | 7/1980 | Okazaki et al. | |
| 4,479,495 | A * | 10/1984 | Isaacson | 606/204 |
| 5,284,272 | A * | 2/1994 | Wei | 222/192 |
| 5,695,520 | A * | 12/1997 | Bruckner et al. | 606/204 |

(Continued)

FOREIGN PATENT DOCUMENTS

EP 0 181 676 A1 5/2010

*Primary Examiner* — Tuan V Nguyen
*Assistant Examiner* — Tin Nguyen
(74) *Attorney, Agent, or Firm* — Skaar Ulbrich Macari, P.A.

(57) ABSTRACT

Disclosed are neuromuscular release (including myofascial trigger point) therapy devices, systems, kits and methods. The therapy tool comprises a body, wherein the body includes an outer surface, an inner surface, a tip defined at the upper-most portion of the body, a base, a stop surface defined in the body outer surface, a pocket defined by the inner surface and extending from the base upwards in the direction of the tip, and a recessed groove defined in the inner surface and extending upwards from the base and having a groove diameter and depth. The body can be generally bell-shaped with the base having a larger diameter than the tip. The system can further include a riser, either disk or wedge shaped, and a rocker base. The system components are configured to stack and nest into a compact assembly for easy carrying as a kit.

11 Claims, 21 Drawing Sheets

(56) References Cited

U.S. PATENT DOCUMENTS

| | | | |
|---|---|---|---|
| 5,820,573 A | | 10/1998 | Ramos |
| 6,013,042 A | | 1/2000 | Sakai |
| 6,126,085 A | * | 10/2000 | Wanzenbock .................. 239/36 |
| 6,821,260 B2 | | 11/2004 | Fors |
| 6,921,372 B2 | | 7/2005 | Shin |
| 7,320,668 B1 | | 1/2008 | Warder |
| D586,470 S | | 2/2009 | Warder |
| 2001/0041851 A1 | | 11/2001 | Peyton et al. |
| 2002/0049469 A1 | | 4/2002 | Chang |
| 2002/0068888 A1 | | 6/2002 | Wang et al. |
| 2008/0086066 A1 | | 4/2008 | Munday |
| 2010/0145244 A1 | | 6/2010 | Schwartz et al. |
| 2010/0252564 A1 | * | 10/2010 | Martinez et al. .............. 220/796 |

* cited by examiner

NEUROMUSCULAR RELEASE THERAPY DEVICE, SYSTEM AND METHODS

PRIORITY

This application claims priority to U.S. Provisional Patent Application No. 61/379,924, filed Sep. 3, 2010, which is hereby incorporated herein by reference in its entirety.

FIELD

The present invention relates to neuromuscular release (including myofascial trigger point) therapy devices, systems and methods. More particularly, the present invention relates to compact, modular and adjustable neuromuscular release devices, systems and methods.

BACKGROUND

Neuromuscular release (including myofascial trigger point) (hereinafter generally referred to as "trigger point") therapy is a method of treating pain that is popular and gaining in popularity; it is commonly used by physical and massage therapists, osteopaths and chiropractors to treat musculoskeletal pain. It comprises the sustained pressure of the hand, finger(s), knee, elbow, foot, or tool on a myofascial trigger point ('trigger point'), a localized and usually exquisitely tender area in a tendon or muscle that "triggers" the pain felt by the sufferer. The location of the trigger point can coincide with the perceived pain, or can be distant (referred pain). When pressure is applied to the trigger point, the perceived pain usually increases in intensity briefly, and then with continued sustained pressure gradually starts to dissipate until it completely disappears. This process usually takes 20 to 90 seconds and is dependent on the intensity and duration of the pain, the depth and acuity of the pressure applied, as well as the familiarity of the sufferer with this form of treatment and the need to actively relax the area, partially by using deep, relaxing breathing. The effect of the pain relief is usually prolonged by the utilization of stretching exercises performed in the muscle-tendon unit involved immediately after the trigger point release intervention, and postural correction exercises aimed at preventing the recurrence of the pain. Repeating this process on a regular basis helps to prevent pain recurrence until ergonomic and postural corrections take effect.

The pain sufferer will also benefit from more frequent use of such interventions. The pain sufferer would do well to use self-treatment tools on a regular basis (daily or every other day) to maintain musculotendinous units in their normal functioning status, rather than being dependent on frequent and expensive visits to a medical professional for formal interventions of this nature.

Conventionally available to permit individuals to self-treat myofascial trigger points are tools, including canes, balls and rollers, board-mounted probes, and hand-held probes.

Canes are used to apply pressure to a trigger point and most areas of the body are accessible by the user. However, the user must apply pressure to the point with sufficient pressure to "release" the trigger point, but also within comfort levels, while simultaneously relaxing the area being treated. This can be a difficult process, particularly when treating areas in or around the upper extremities which are being used to exert the force. In some cases, a cane can be used as a lever; the user would lie on the tip of the cane and then rotate the handle to apply force at the tip into the trigger point. In this instance, the user still needs to apply exertion to the tool to effect the desired pressure, which can be neurologically confusing, since the user is attempting to relax the area (a process of inhibiting neural activation at the level of the spinal cord) while exerting force (a process of stimulation at the level of the spinal cord). Canes are bulky and unwieldy instruments and are conspicuous in professional or office situations. Only a few of the uses of the cane are intuitive, and the user is reliant on an owner's manual to learn to use the cane to treat difficult-to-reach places. Commercially available canes include the Thera Cane™, The BackKnobber™ and The Body Back Buddy™.

Balls and rollers have a broad contour, which can be sub-optimal in reaching a specific trigger point and it can be difficult to modulate the intensity of the pressure applied to the trigger point. Various balls including tennis, golf, lacrosse and racket balls are used. Commercially available balls include the Trigger Point Massage Ball™ and the Myo-Therapy Ball™. Commercially available bands include the Trigger Point Quadroller™. When desiring to penetrate deeper into the area of a trigger point, the sufferer would look to use a larger ball, which in turn has a larger contour. The dilemma of using a ball therefore results in a decision regarding depth and acuity, and the sufferer cannot have both with this choice.

Hand-held probes are effective in treating pain using the myofascial trigger point release techniques but, for self-treatment, certain areas of the body are difficult or impossible to reach effectively, rendering the user dependent on a helper, or frustrated at being unable to adequately reach an awkward area. In addition, in similar fashion to the cane, self-treatment may require one set of muscles to be activated (to apply the pressure) while the sufferer is simultaneously attempting to relax the affected area. This is particularly difficult when the muscle groups are in close proximity, as described above. This often leaves the user frustrated at the inadequacy of the tool, which is unfortunate since it is rather the circumstances of the tool's use that is inadequate. Some hand-held probes can be used to relieve pain with the user lying on the probe. However, the probe's height and angle and, depending on the design of the tool, the contour are fixed and, as a result, the probe may be too high or low, too large or small, or at an inconvenient angle relative to the trigger point being treated, especially when pressure is applied to the thin muscle overlying the ribs in a lean user, or to the occiput. Commercially available probes include the Hand-L™, the Jackknobber™ and the Knobbler™.

The board mounted systems comprise a platform and rubber tips covering various lengths of dowel that can be inserted into the board at varying angles. This affords the user the ability to select the number, angle, position and height of the probe(s). The probes have various contours (diameter of the probe). Board devices are cumbersome and conspicuous and the many and varied choices of operation can be daunting and confusing. People who have used these systems have commented favorably about the benefit of being able to lie on the device without exerting force, thereby enhancing the relaxation effects of the tool. Commercially available systems include: the Fenix Rehab System™ and the Recapitulator™.

However, there remains a need for a trigger point therapy device, system and method that allows an individual the ability to self-treat trigger points completely independently in a fashion that fosters complete relaxation, as may be the case when the user is able to lie on or lean against the tool or device, which provides the user simple choices in terms of size and height, and which is easily transported and used in conspicuous areas, such as in an office.

SUMMARY

An objective of the present invention is to provide a trigger point therapy device, system, kit and method. In one embodiment, the trigger point therapy system comprises a tool. The tool comprises a body, wherein the body includes an outer surface, an inner surface, a tip defined at the upper-most portion of the body, a base, a stop surface defined in the body outer surface, a pocket defined by the inner surface and extending from the base upwards in the direction of the tip, and a recessed groove defined in the inner surface and extending upwards from the base and having a groove diameter and depth. The body can be generally bell-shaped with the base having a larger diameter than the tip. The system can further include a riser, either disk or wedge shaped, and a rocker base. The system components are configured to stack and nest into a compact assembly for easy carrying as a kit.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

DETAILED DESCRIPTION

Figure 1:
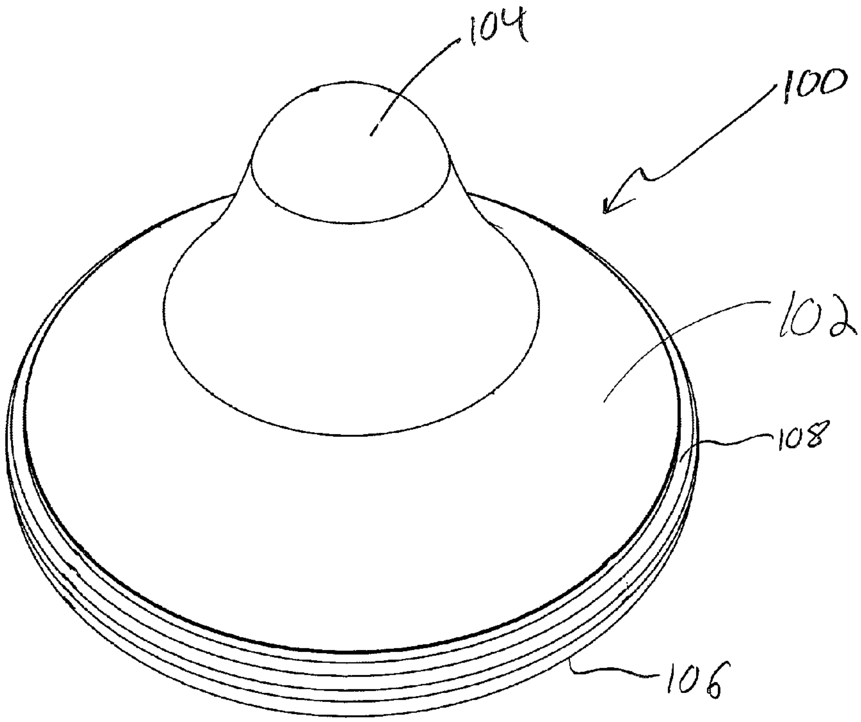
FIG. 1 is a perspective view of a neuromuscular release therapy device according to certain embodiments.
Figure 2:
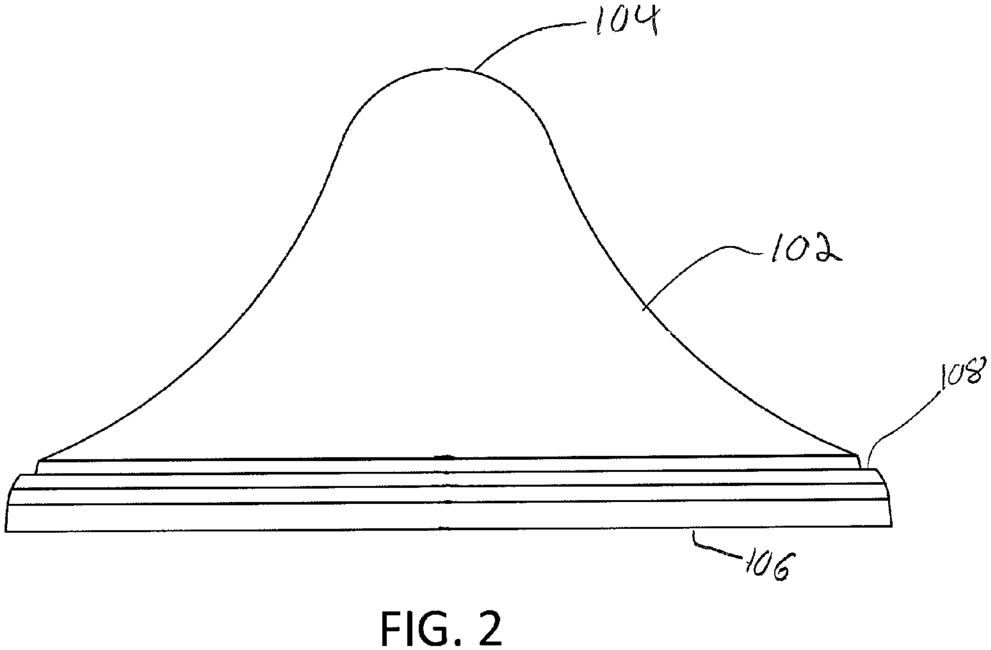
FIG. 2 is a side view of a neuromuscular release therapy device according to certain embodiments.
Figure 3:
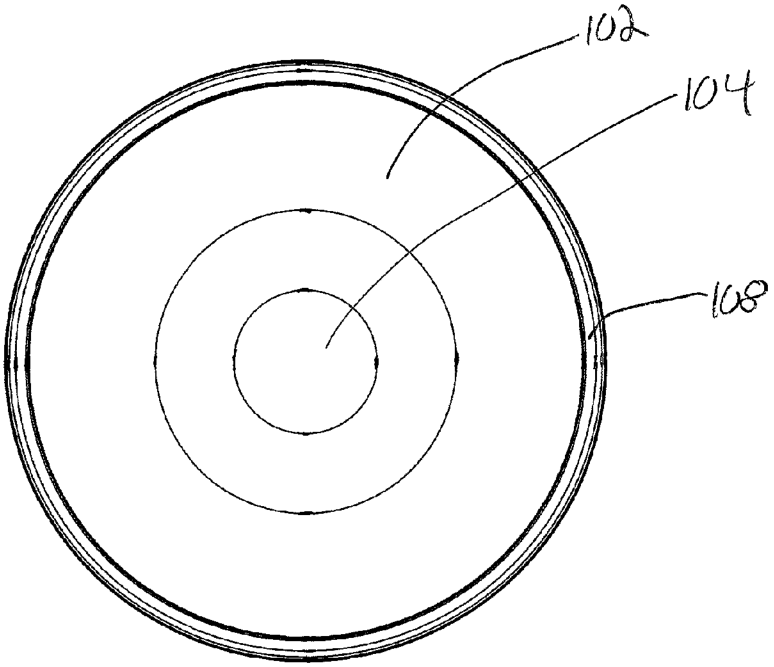
FIG. 3 is a top view of a neuromuscular release therapy device according to certain embodiments.
Figure 4:
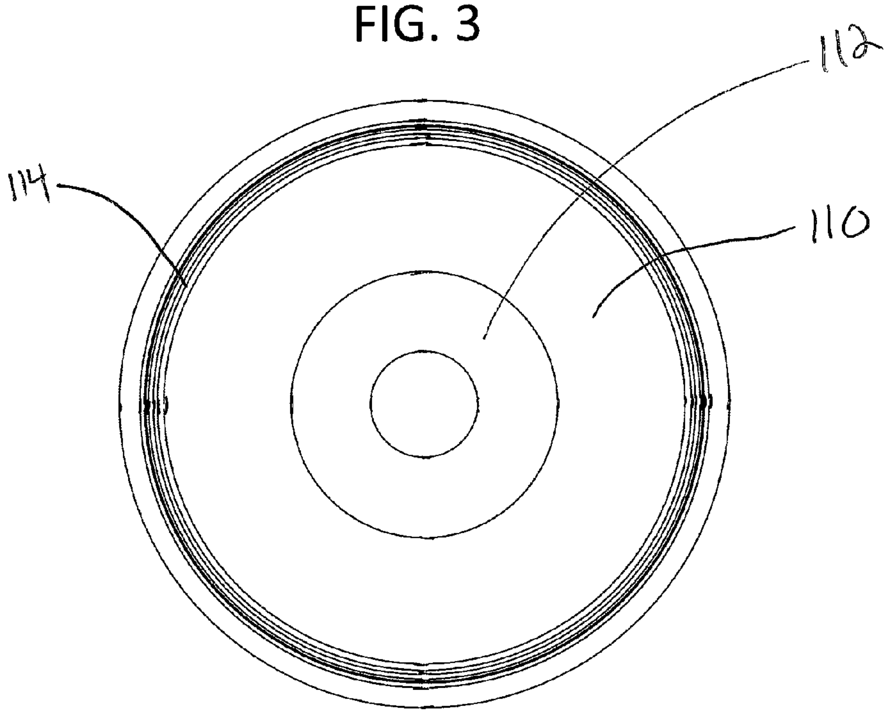
FIG. 4 is a bottom view of a neuromuscular release therapy device according to certain embodiments.
Figure 5:
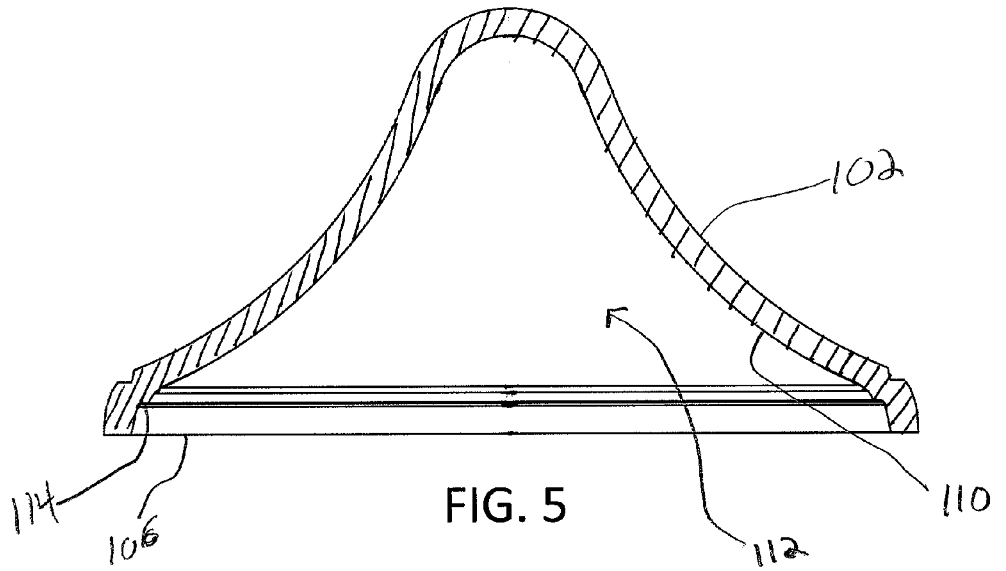
FIG. 5 is a cross-sectional side view of a neuromuscular release therapy device according to certain embodiments.
Figure 6:
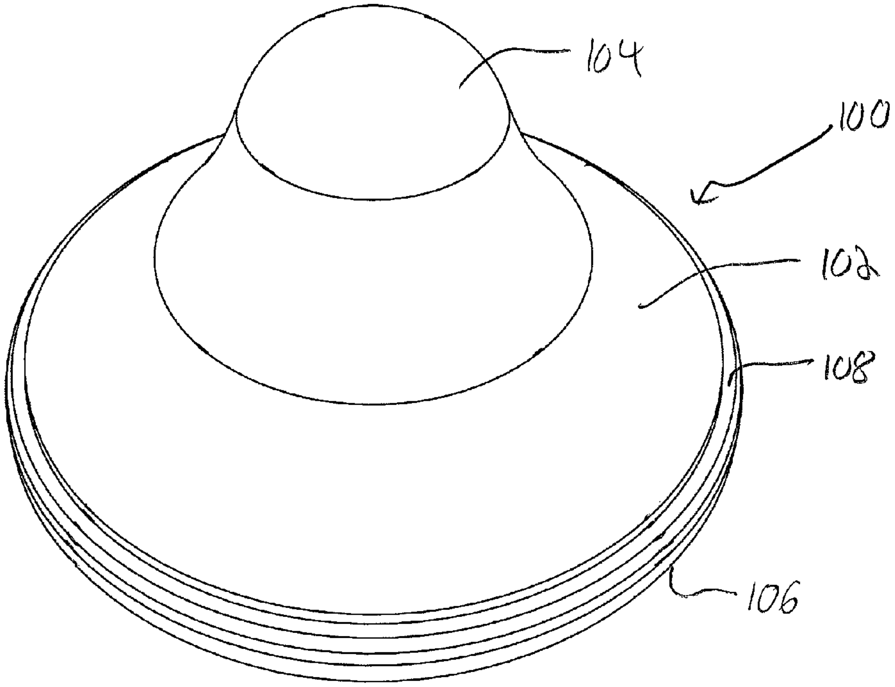
FIG. 6 is a perspective view of a neuromuscular release therapy device according to certain embodiments.
Figure 7:
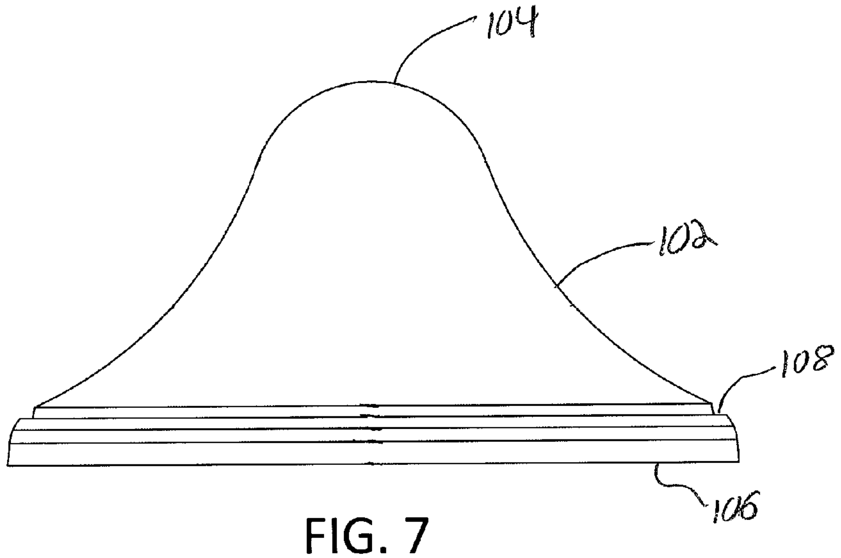
FIG. 7 is a side view of a neuromuscular release therapy device according to certain embodiments.
Figure 8:
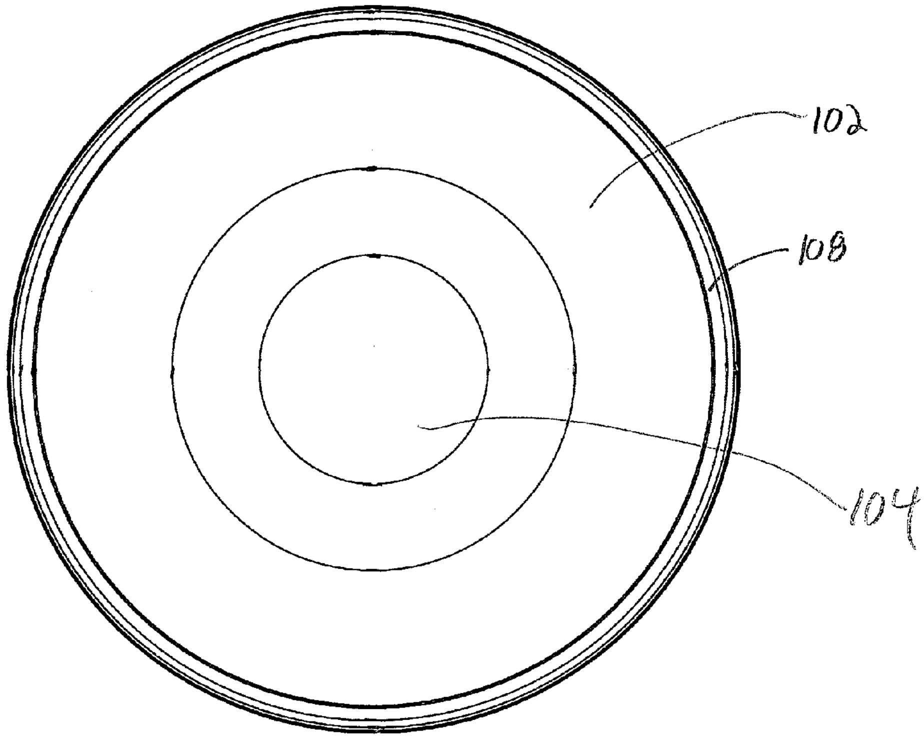
FIG. 8 is a top view of a neuromuscular release therapy device according to certain embodiments.
Figure 9:
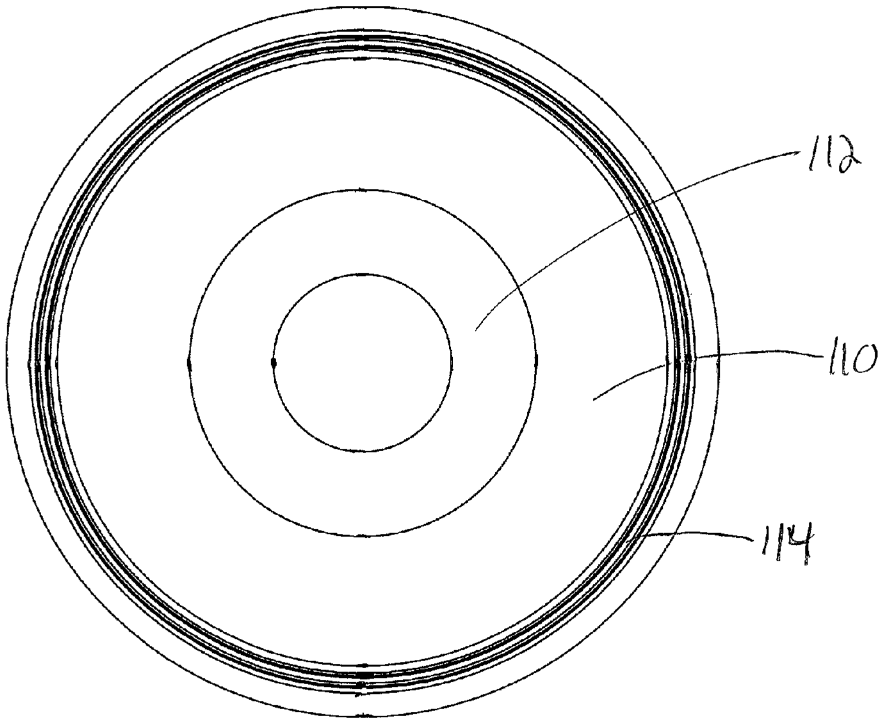
FIG. 9 is a bottom view of a neuromuscular release therapy device according to certain embodiments.
Figure 10:
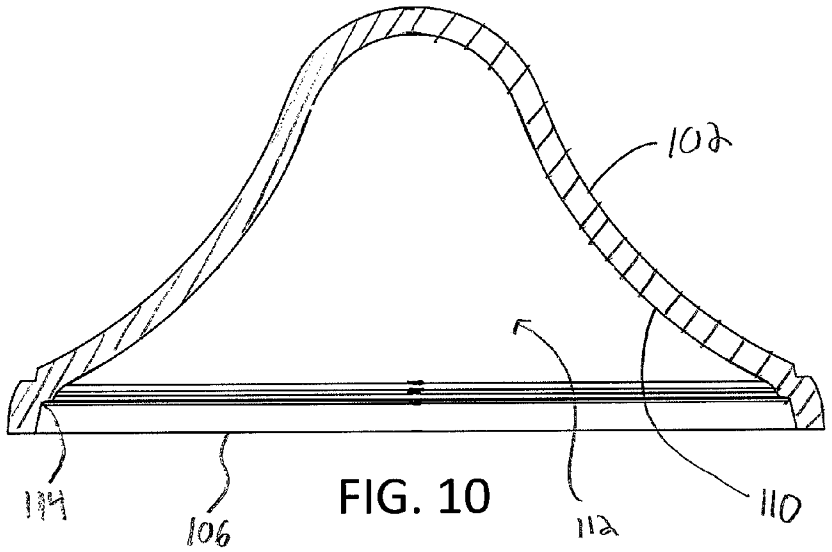
FIG. 10 is a cross-sectional side view of a neuromuscular release therapy device according to certain embodiments.
Figure 11:
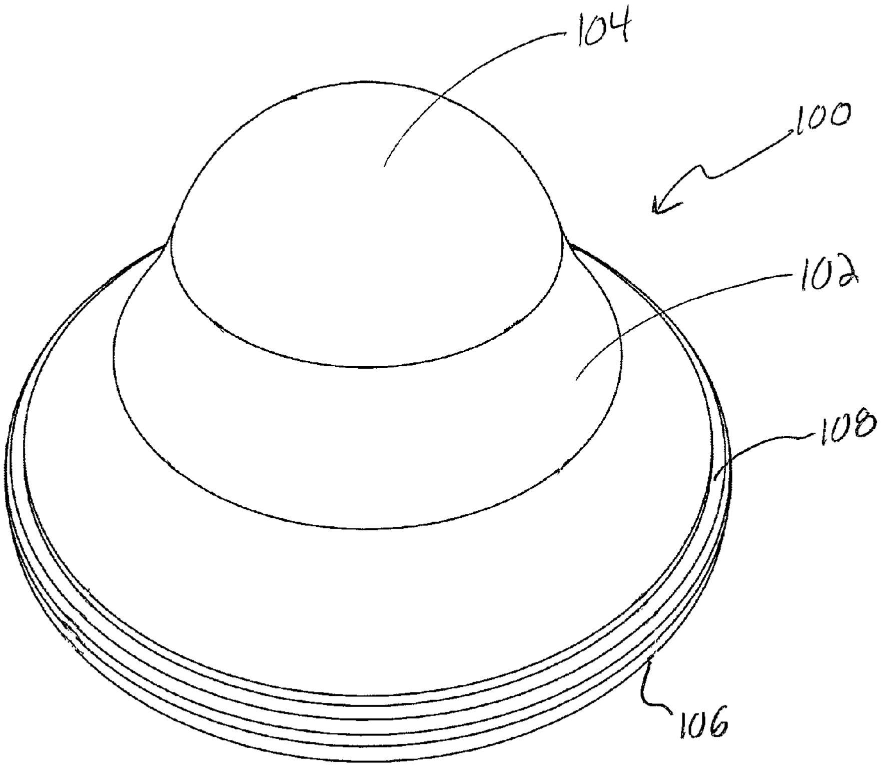
FIG. 11 is a perspective view of a neuromuscular release therapy device according to certain embodiments.
Figure 12:
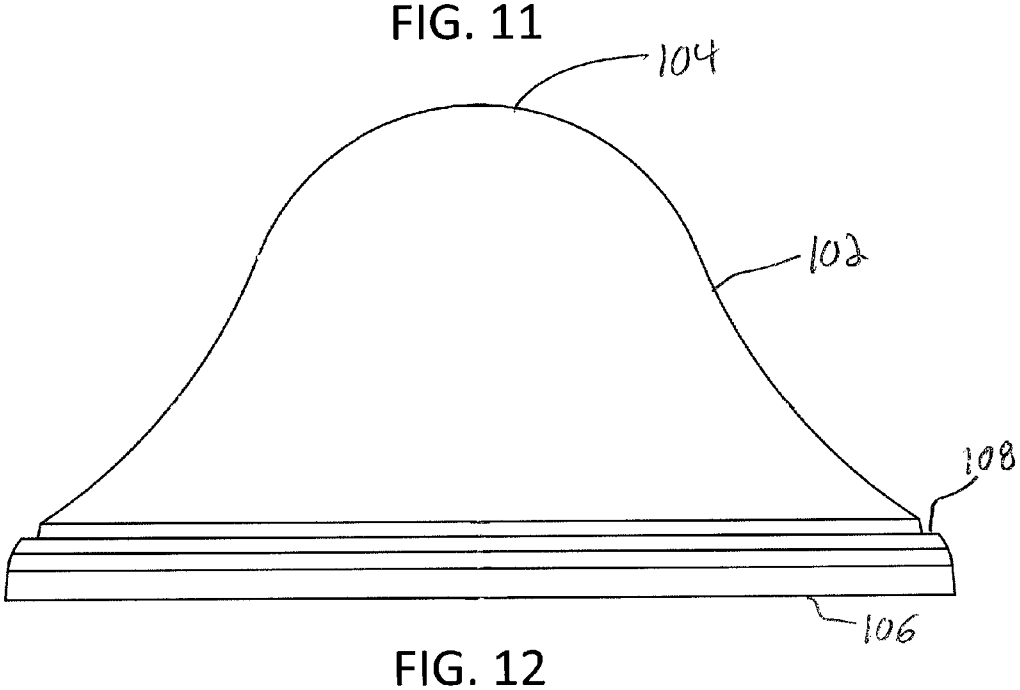
FIG. 12 is a side view of a neuromuscular release therapy device according to certain embodiments.
Figure 13:
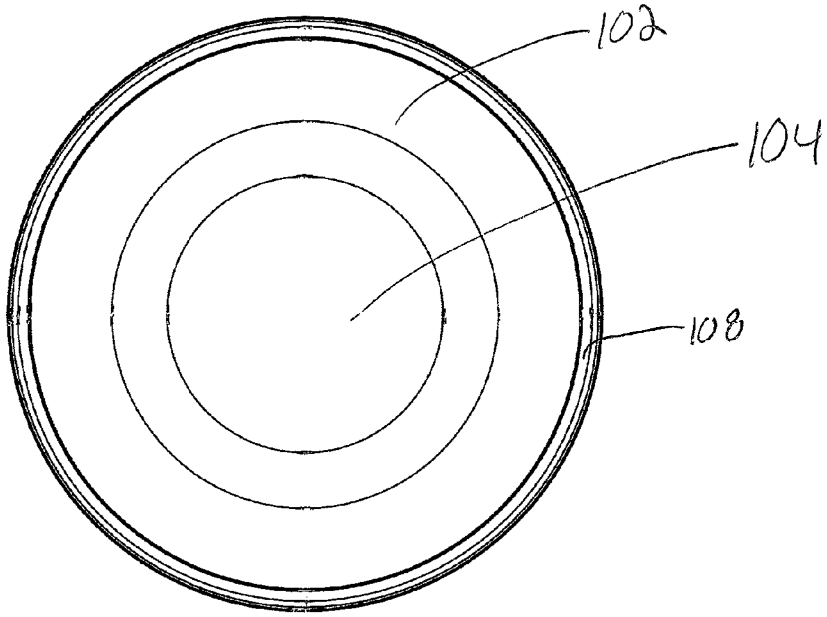
FIG. 13 is a top view of a neuromuscular release therapy device according to certain embodiments.
Figure 14:
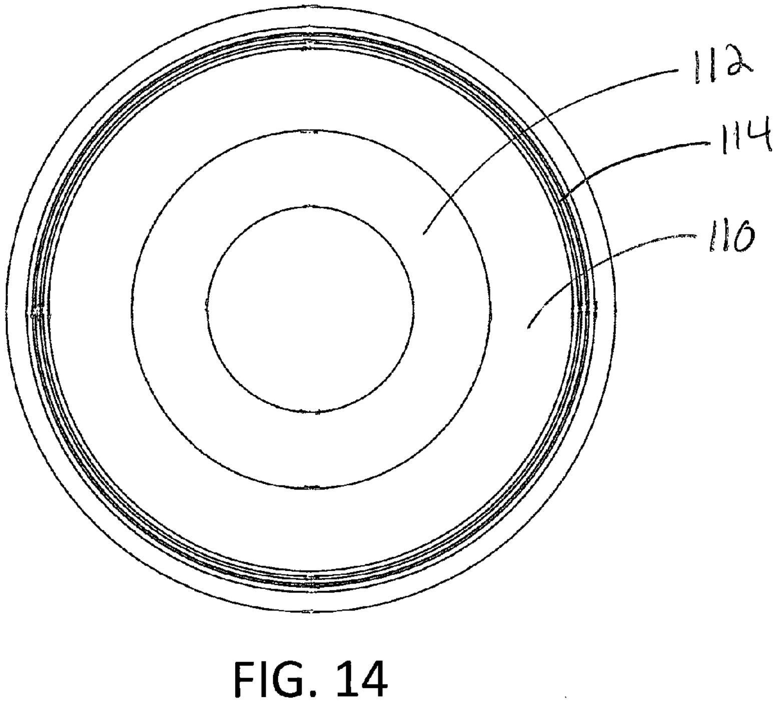
FIG. 14 is a bottom view of a neuromuscular release therapy device according to certain embodiments.
Figure 15:
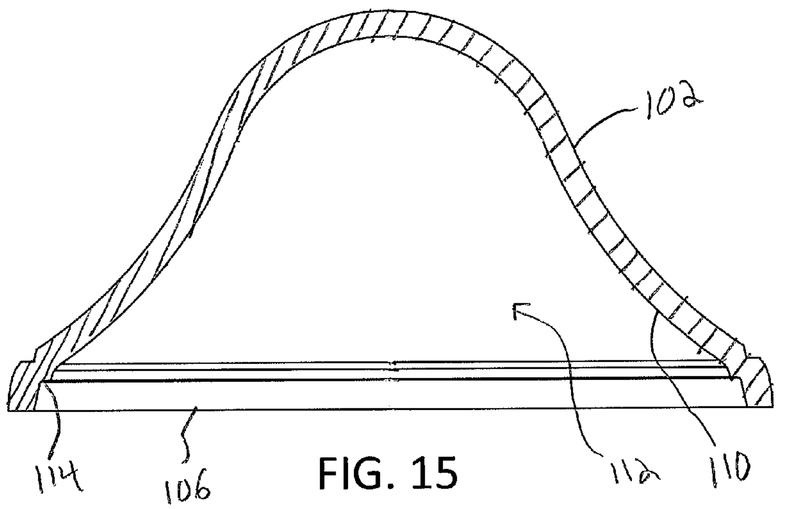
FIG. 15 is a cross-sectional side view of a neuromuscular release therapy device according to certain embodiments.
Figure 16:
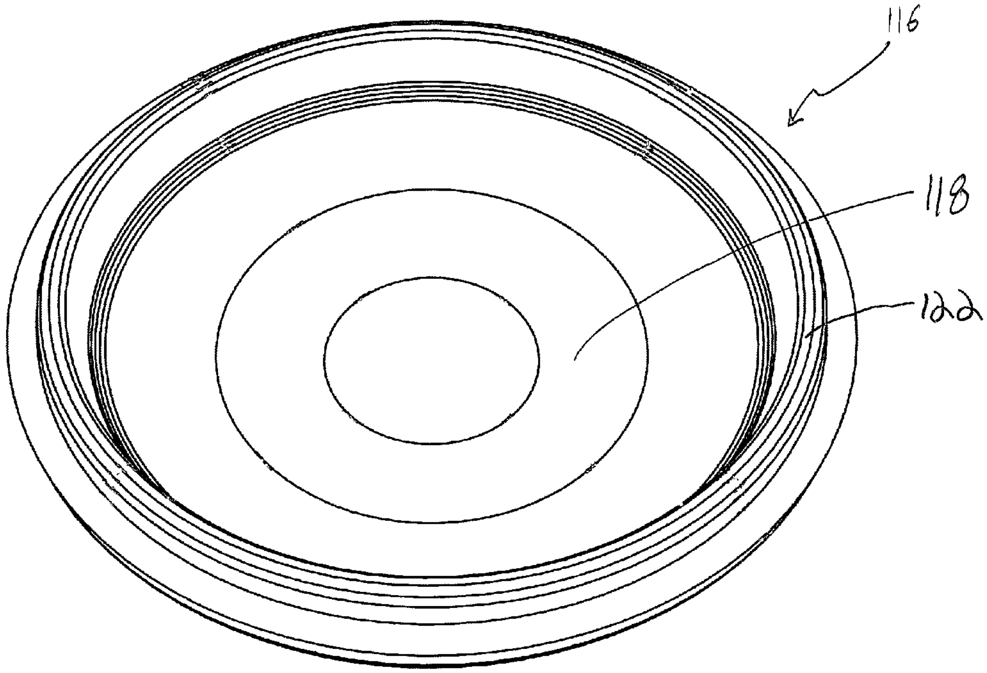
FIG. 16 is a perspective view of a base for a neuromuscular release therapy device according to certain embodiments.
Figure 17:
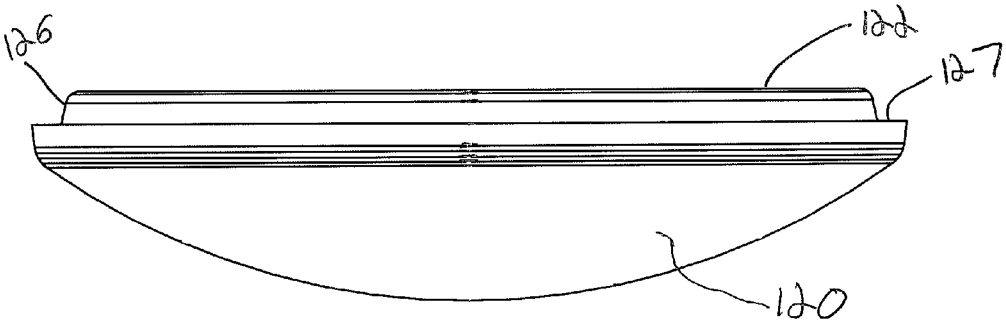
FIG. 17 is a side view of a base for a neuromuscular release therapy device according to certain embodiments.
Figure 18:
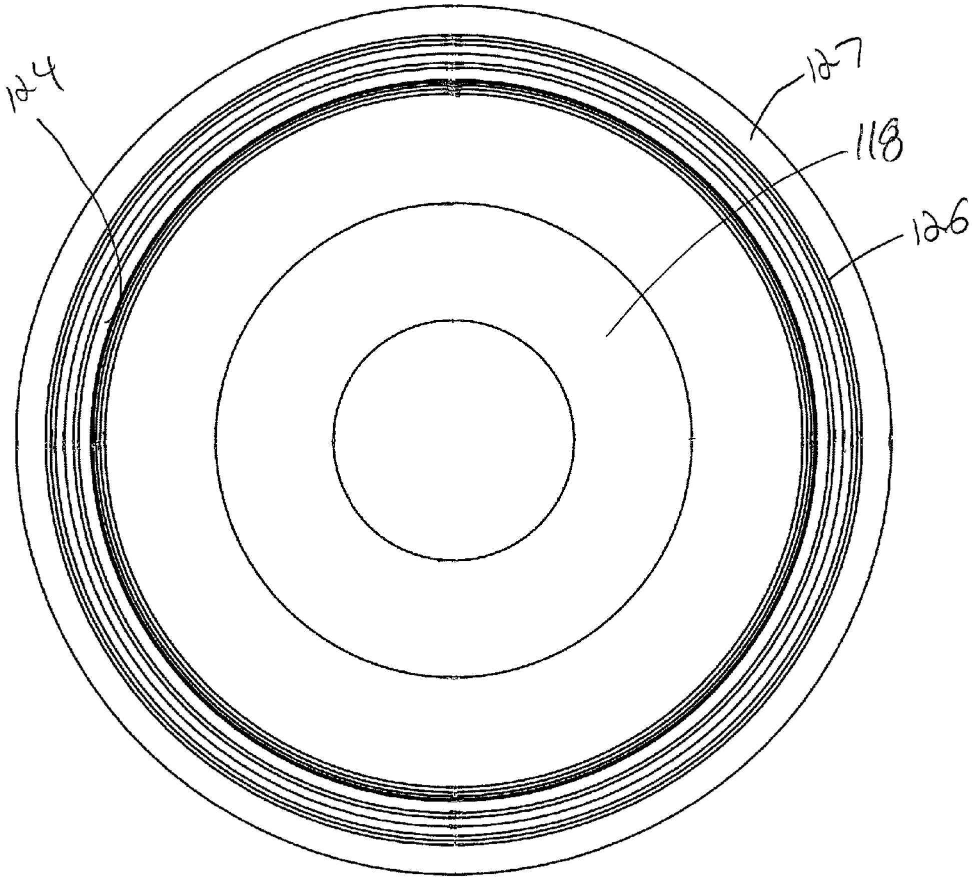
FIG. 18 is a top view of a base for a neuromuscular release therapy device according to certain embodiments.
Figure 19:
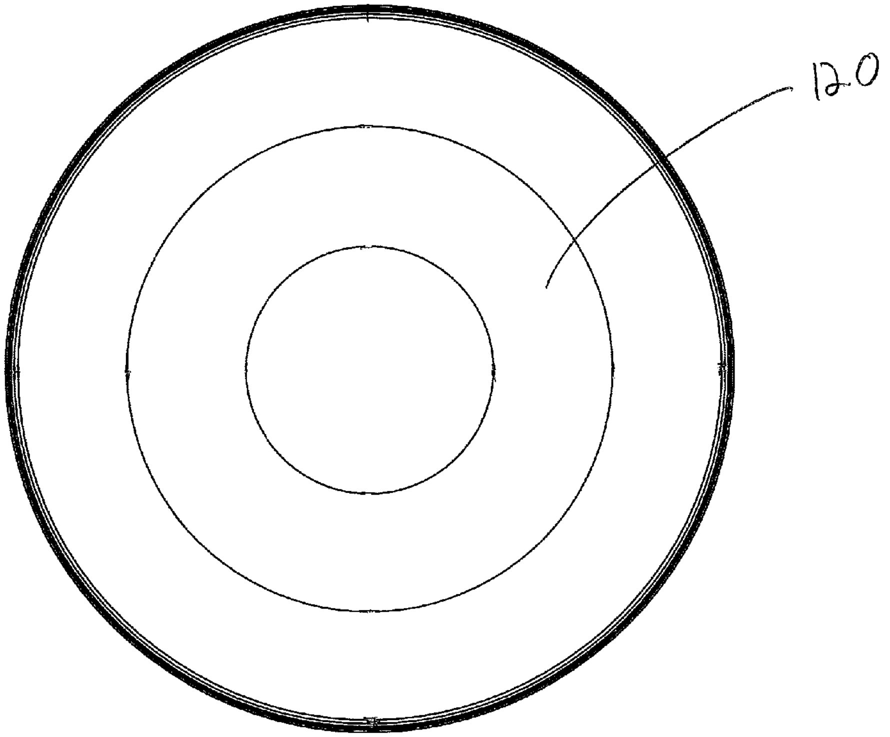
FIG. 19 is a bottom view of a base for a neuromuscular release therapy device according to certain embodiments.
Figure 20:
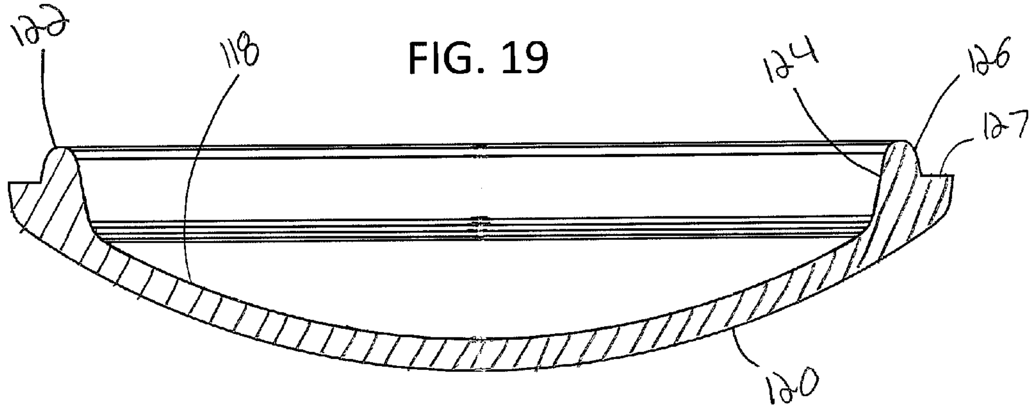
FIG. 20 is a cross-sectional side view of a base for a neuromuscular release therapy device according to certain embodiments.
Figure 21:
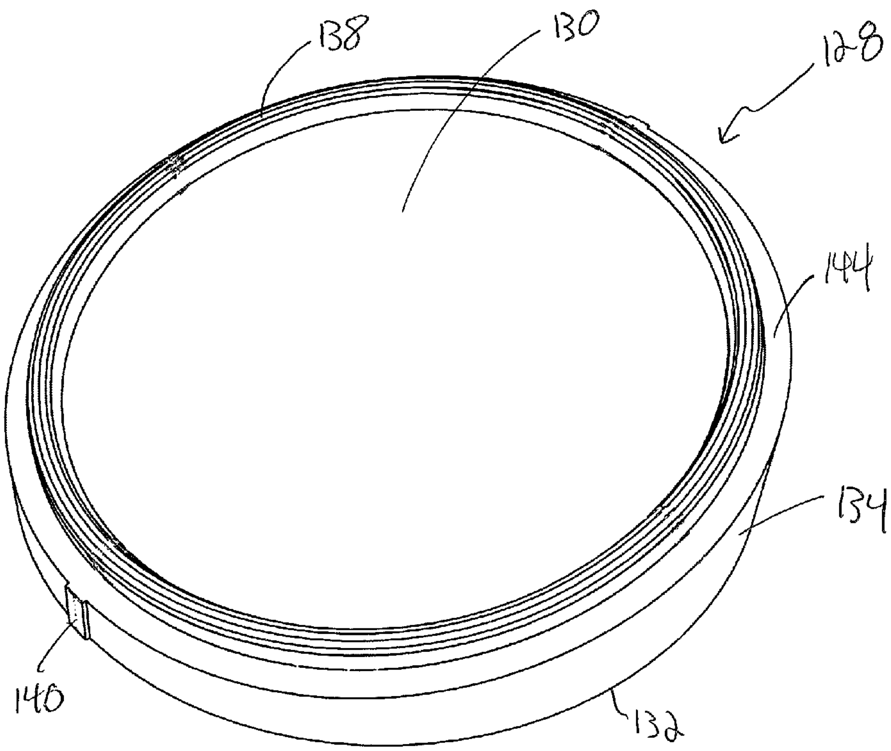
FIG. 21 is a perspective view of a base for a neuromuscular release therapy device according to certain embodiments.
Figure 22:
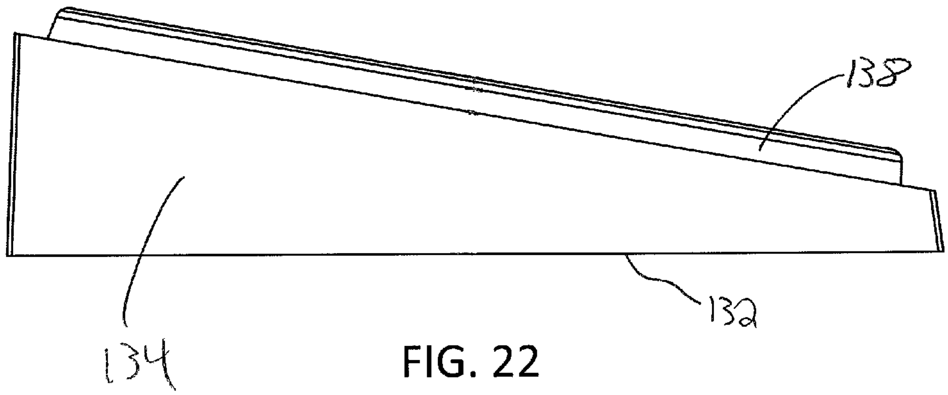
FIG. 22 is a side view of a base for a neuromuscular release therapy device according to certain embodiments.
Figure 23:
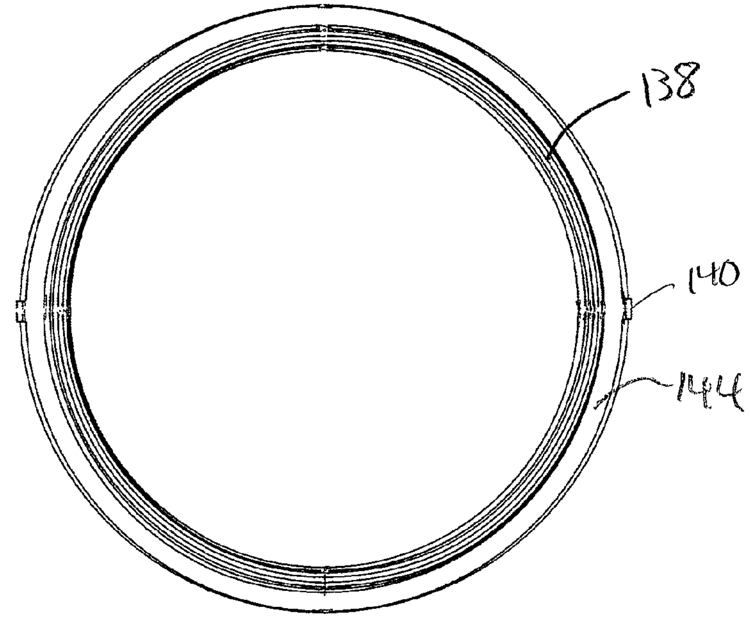
FIG. 23 is a top view of a base for a neuromuscular release therapy device according to certain embodiments.
Figure 24:
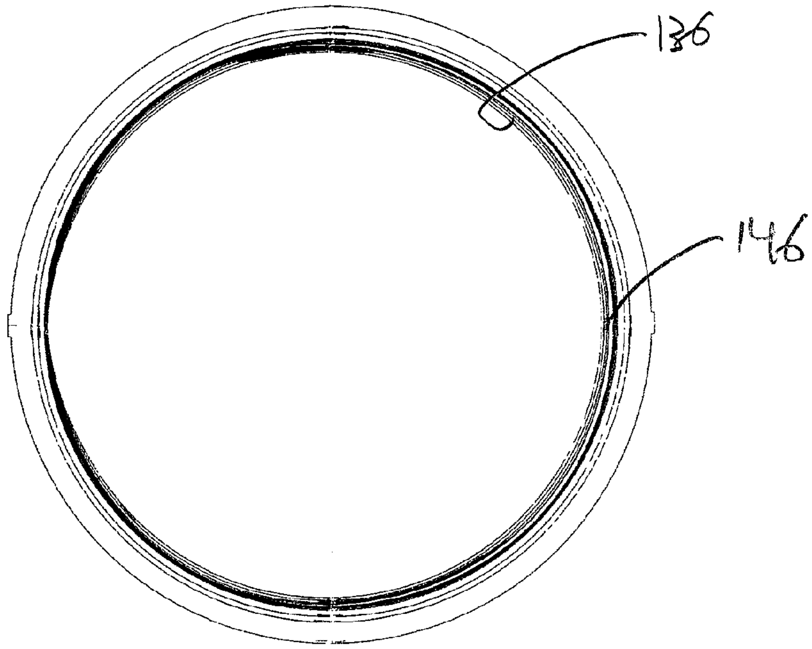
FIG. 24 is a bottom view of a base for a neuromuscular release therapy device according to certain embodiments.
Figure 25:
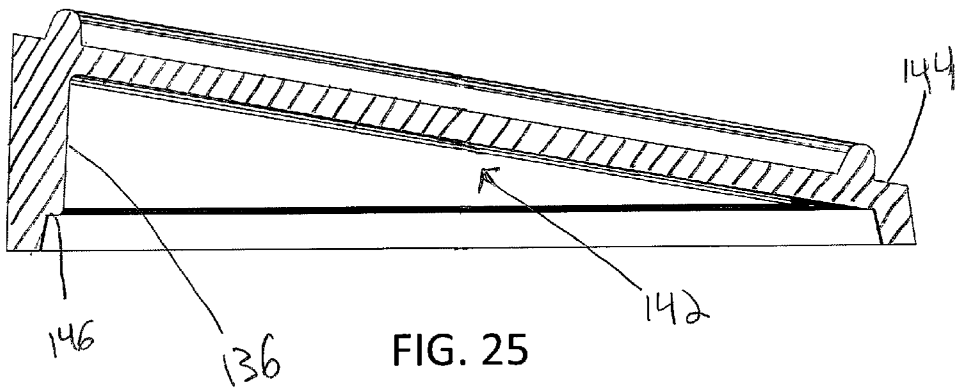
FIG. 25 is a cross-sectional side view of a base for a neuromuscular release therapy device according to certain embodiments.

In the following descriptions, the present invention will be explained with reference to example embodiments thereof. However, these example embodiments are not intended to limit the present invention to any specific example, embodiment, environment, applications or particular implementations described in these example embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Referring first to FIGS. 1-5, a trigger point therapy tool 100 is shown. The tool comprises a body 100 including an outer circumferential surface 102 that generally resembles a cone.

However is can be seen in cross-section that the outer surface is substantially sinusoidal or bell-curved. It should be understood that the surface profile can be straight ribbed or varied in other manners without departing from the scope of the invention. The top or upper most portion the tool 100 presents a rounded tip 104. The tip can be rounded as shown, polyhedral or other suitable shape for applying therapy to the patient. The bottom portion of the tool 100 forms a base 106. The base is wider than the diameter of the tip. The base profile can also be varied, such as circular, as shown in the drawings, square, polyhedral, or another shape, without departing from the scope of the invention.

Adjacent the base is a groove or stop surface 108 that circumscribes the outer surface. The stop surface 108 functions as an engaging surface for additional components of a system or kit as will be described later in this specification. The stop surface 108 may be flat or horizontal plane. However other orientations and shapes can be used that accomplish the function as will be described later herein.

The tool 100 further comprises an inner surface 110. The inner surface 110 is recessed upwards form the plane of the base 106 to form a pocket 112. The pocket provides clearance for stacking multiple components as will be described later. The recess also reduces the volume of material needed to form the tool 100. By doing so, the weight and cost of the tool 100 are reduced.

The inner surface 110 further can include a recessed groove 114. The recessed groove circumscribes the inner surface 110 and is shaped and sized complimentary to the stop surface 108 to facilitate stable stacking of various system components.

FIGS. 6-10 and 11-15, respectively, illustrate additional example embodiments of the tool 100. FIGS. 6-10 show the tip 104 being of a larger radius than the one shown in FIGS. 1-5. FIGS. 11-15 show the tip 104 being of a larger radius than the one shown in FIGS. 6-10. Increasing the tip radius spreads the force of the tool over a larger area, thereby reducing the penetration of the tool force felt by the patient. Conversely, reducing the tip radius increases the penetration felt by the patient. Tool tips of up to 3 inches in diameter have been found to be suitable. In such example, the base width would be correspondingly up to 4 inches. Example tip sizes are ⅜ inch, ½ inch and ¾ inches. However, all of the dimensions herein are merely exemplary and are not intended to restrict the dimensions or scale of the invention, except where specific dimensions are explicitly recited in the claims.

Tools can be marked with an indication of the penetration force, e.g. Regular, Strong and Extra Strong, or color coded to aid the patient in selecting the correct tool or differentiating more easily between tools of differing strengths.

Referring now to FIGS. 16-20, a rocker base tool 116 is shown. The rocker base tool 116 comprises a dished upper surface 118 and a rounded or concave bottom surface 120. The upper surface 118 of the rocker base 116 is generally planar or other orientation that is complimentary to the plane of the base surface 106 of the therapy tool 100 and complimentary to the plane of the bottom surfaces of other system components that will be described in this specification. A flange 122 can extend upwards from the upper surface 118. The flange 118 is generally circumferential and includes an inner circumferential surface 124 and an outer circumferential surface 126. The height of the flange 122 is approximately the same as the depth of the recessed groove 114 in the tool 100 or the recessed groove in the other system components. The diameter of the outer circumferential surface 126 is approximately the same as the circumferential diameter of the recessed groove 114 in the tool 100 or the recessed groove in the other system components. An upwardly facing stop surface 127 portion of the top surface extends outwardly of the outer surface of the flange 122. Thus stacking of various components is facilitated. The curved bottom surface 120 is generally smooth and contiguous to aid in rocking on various surfaces, including carpeting, flooring, chairs and walls.

Referring to FIGS. 21-25, a wedge base component 128 is shown. The wedge base 128 comprises an upper surface 130, a bottom surface 132, a circumferential outer surface 134 and an inner surface 136. The upper surface 130 is generally planar and is oriented at an acute angle with respect to the plane of the bottom 132. A raised flange or surface 138 extends upwardly from the upper surface to a height approximately the same as the depth of the recessed groove 114 in the tool 100 or the recessed groove in the other system components. The diameter of the flange or raised surface 138 is approximately the same as the circumferential diameter of the recessed groove 114 in the tool 100 or the recessed groove in the other system components. Thus stacking of various components is facilitated. A recessed groove 146 and a stop surface 144 further supports an adjacent component in a stacked configuration.

The outer surface can be provided with a registration indicator 140 to provide an indication to the user of the relative orientation of system components. The inner surface is recessed to form a pocket 142 of sufficient depth and diameter to receive the flange or raised surface 138 of another base 128 or flange 122 of a rocker base component 116.

The upper surface 130 can also be horizontal or parallel to the plane of the bottom surface 132. In such configuration, the wedge forms a riser disk component.

Figure 26:
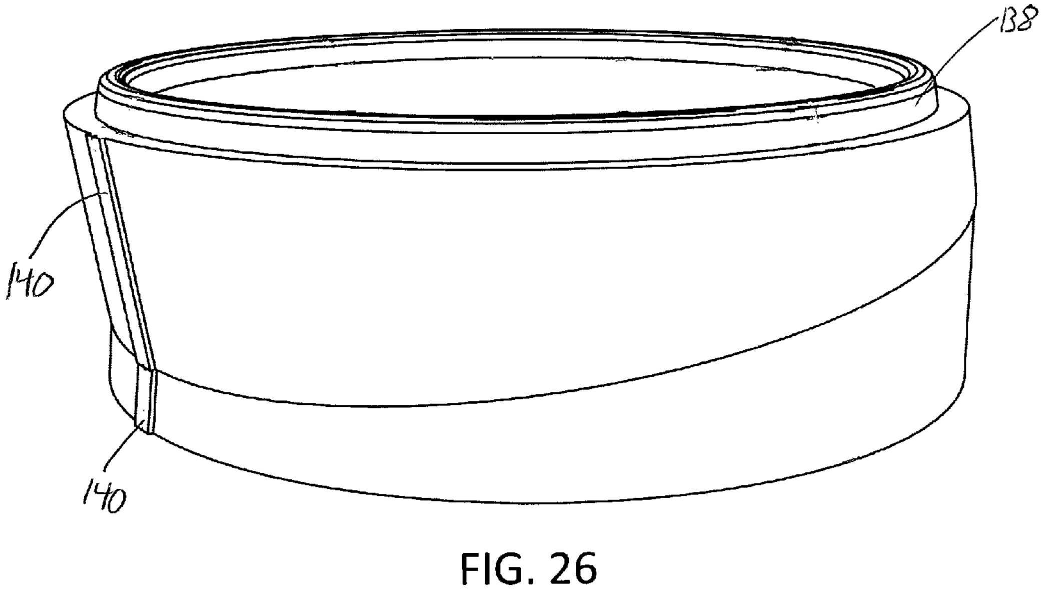
FIG. 26 is a perspective view of stacked bases for a neuromuscular release therapy device according to certain embodiments.
Figure 27:
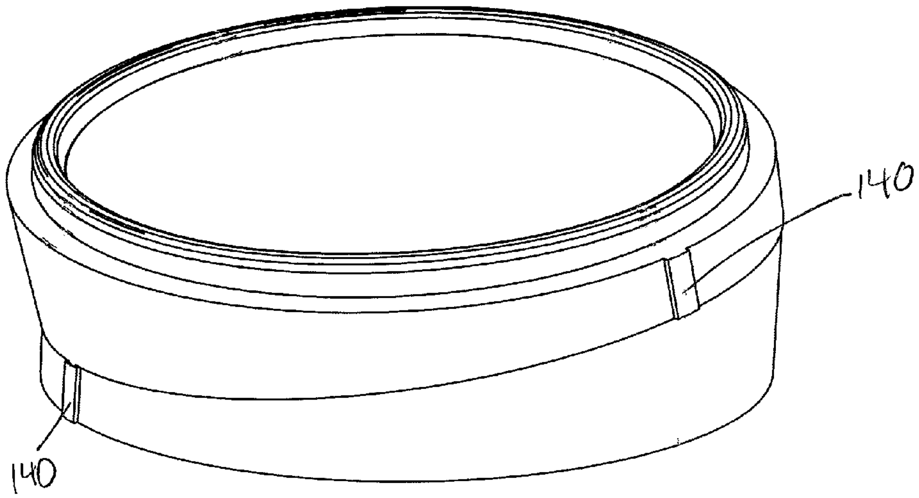
FIG. 27 is a perspective view of stacked bases for a neuromuscular release therapy device according to certain embodiments.

Referring to FIGS. 26-27, two wedge bases 128 are shown in stacked arrangement. In FIG. 26, the top wedge is turned 180 degrees with respect to the rotational orientation of the bottom wedge. The registration indicators are thus aligned. This alignment provides for a raised horizontal surface on which to stack the therapy tool 100. FIG. 27 shows the top wedge turned only ninety degrees relative to the bottom wedge. This can be seen by the top indicator being displaced relative to the bottom indicator by one-quarter turn. As a result, the plane of the top surface is angled with respect to the horizon. Rotating the top wedge further or lesser (between 0 and 180 degrees) will produce a corresponding increase or decrease in the angle with respect to the horizon. Thus the base on which the tool 100 is stacked can be adjusted for angle to suit the penetration angle desired by the user. The curved bottom surface 120 is generally smooth and contiguous to aid in rocking on various surfaces, including carpeting.

Figure 28:
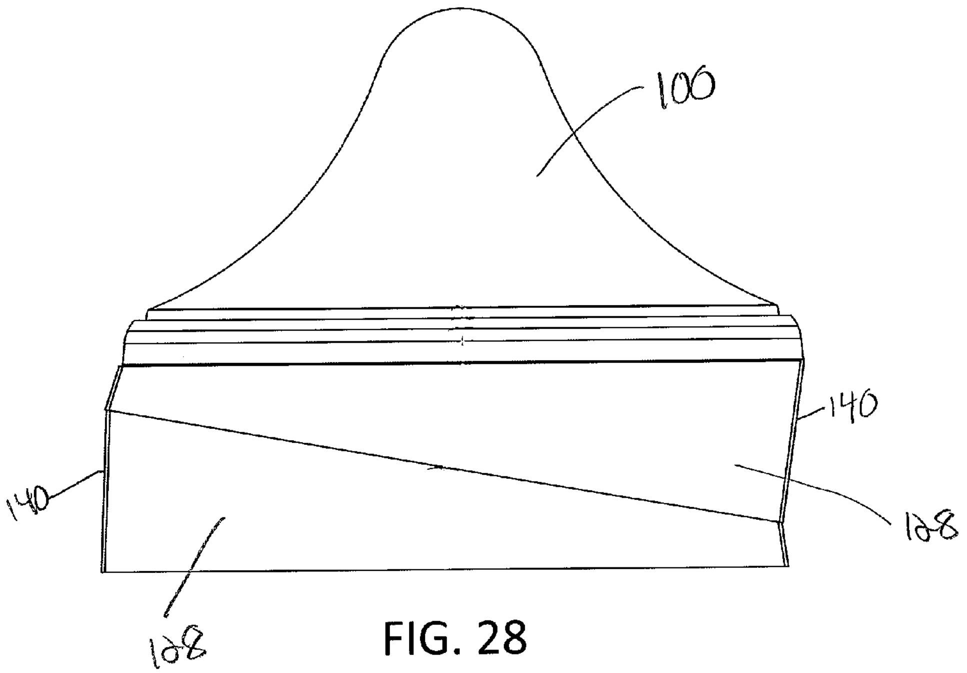
FIG. 28 is a top view of a neuromuscular release therapy device stacked on bases according to certain embodiments.
Figure 29:
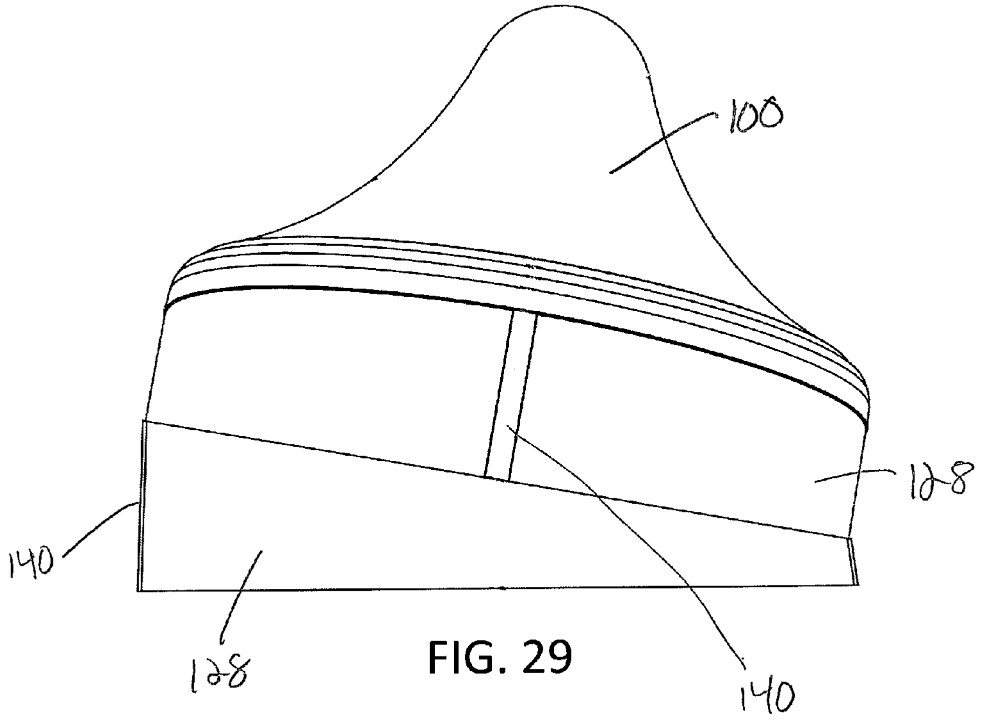
FIG. 29 is a top view of a neuromuscular release therapy device stacked on bases according to certain embodiments.

FIGS. 28 and 29 show the stacked wedges of FIGS. 26-27, respectively, with a tool 100 stacked on top to illustrate the angling function provided by the wedge components as part of a system.

Figure 30:
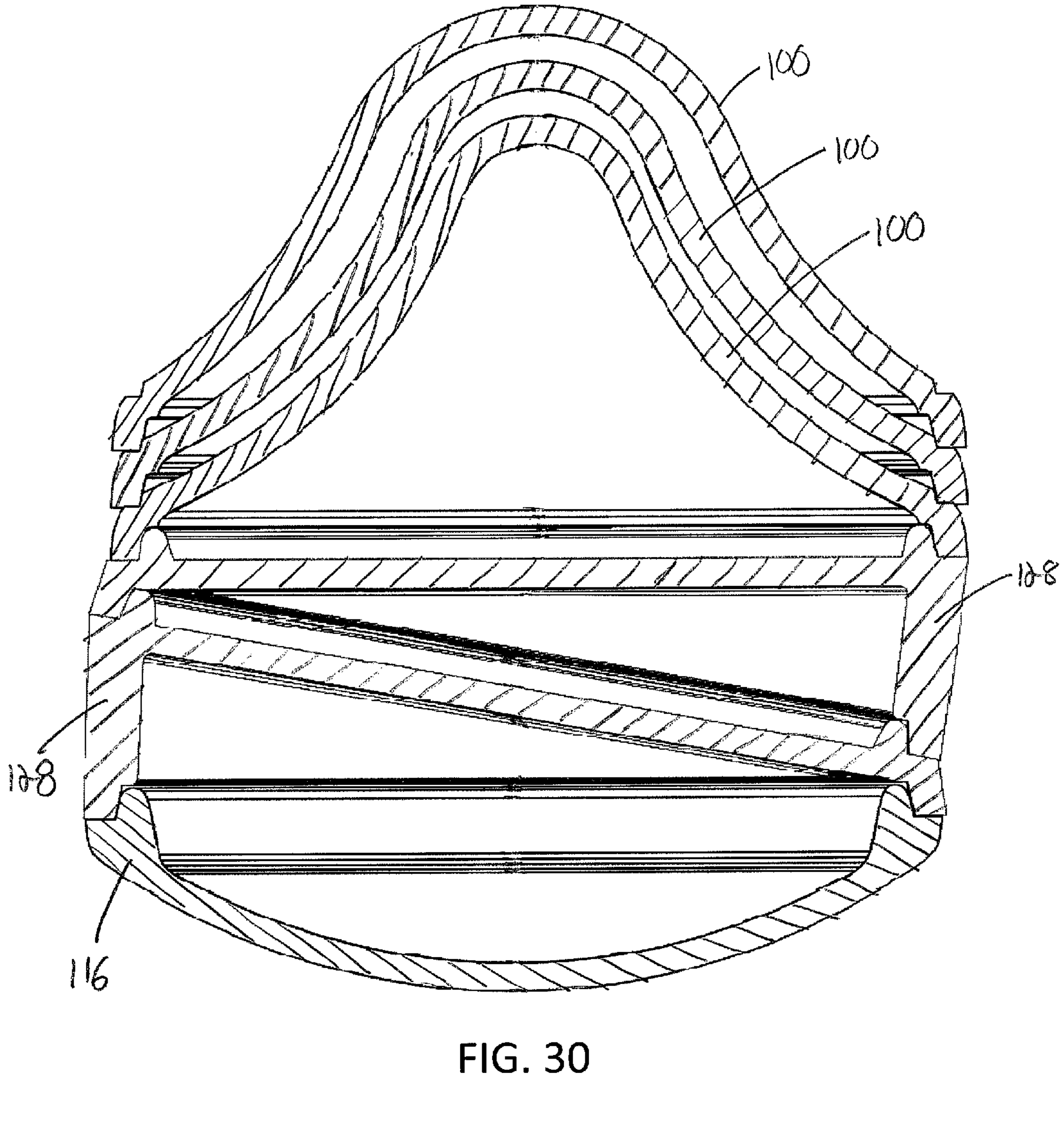
FIG. 30 is a cross-sectional view of a stacked neuromuscular release therapy kit according to certain embodiments.

Referring now to FIG. 30, a system of multiple components is shown in a compact stack to illustrate additional aspects of the invention. The stacked system here includes three therapy tools, wherein each member has a different tip radius, two wedges and a rocker base. The nesting feature of these components can be seen clearly in this figure. The nesting and feature of the respective grooves, stop surfaces and pockets of the various components provides for the compact storage and transport of a collection of components that are referred to as the therapy system 150. The therapy system can include more or fewer components within the scope of the invention. The collection of components can also be referred to as a kit, and may include a set of written instructions and a carrying pouch or bag.

The therapy tools, stacking components and bases described herein can be used to treat trigger points in as many body areas as can be feasibly reached in a reclined (supine, prone, side-lying, or variations of the above), seated or standing positions. It can also be placed between the user and a chair, wall or other firm surface, affording the user the ability to lean against the tool to apply pressure to the trigger point. Adding flat disks (or wedge disks with complimentary registration) increases the height of the probe and acuity of the treatment, adding a sloped disk or disks changes the angle at which the probe can address the area of treatment, which can be varied when two sloped disks are stacked and rotated relative to one-another. It is to be understood that the system and treatment method described herein is not restricted to only the described exemplary uses and methods.

Figure 31:
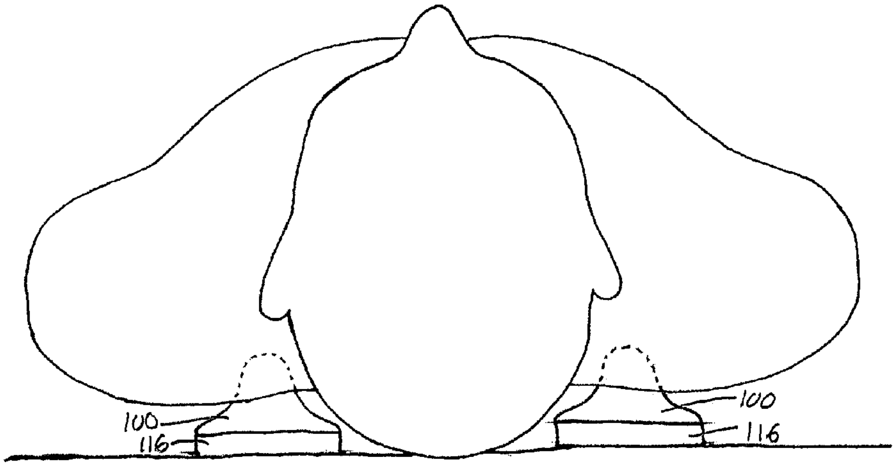
FIG. 31 is an illustration of the use of a neuromuscular release therapy kit according to certain embodiments.
Figure 32:
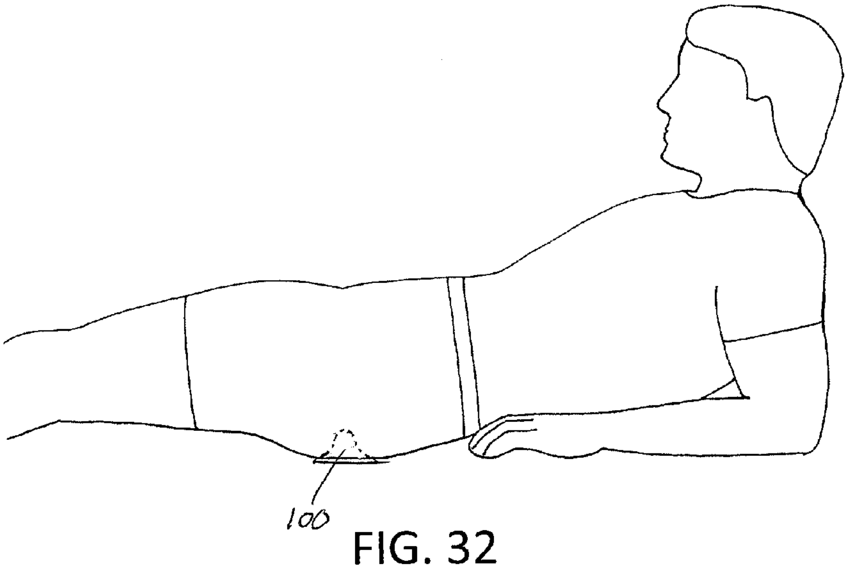
FIG. 32 is an illustration of the use of a neuromuscular release therapy kit according to certain embodiments.
Figure 33:
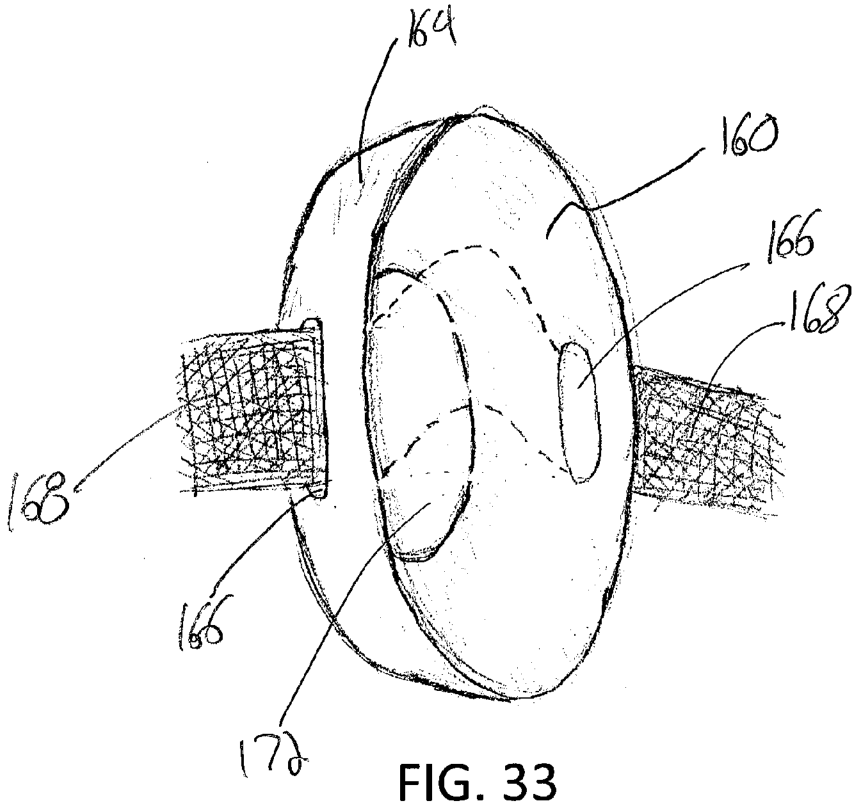
FIG. 33 is a perspective view of a strap attachment ring according to certain embodiments.
Figure 34:
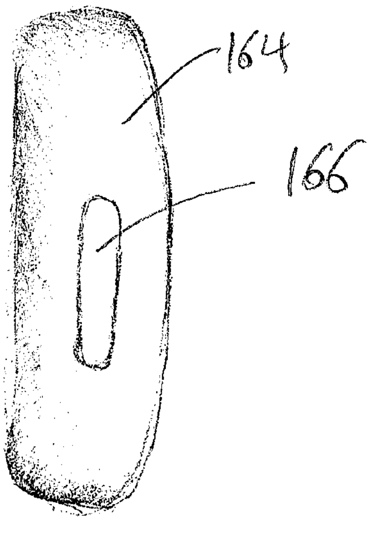
FIG. 34 is a side view of a strap attachment ring according to certain embodiments.
Figure 35:
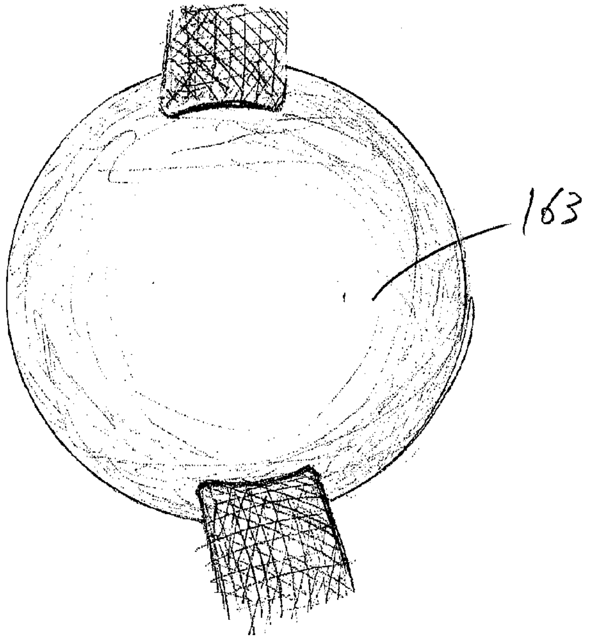
FIG. 35 is a bottom view of a strap attachment ring according to certain embodiments.

Referring to FIG. 31, the tool 100 is shown stacked on one horizontal disk placed on a flat surface, such as a floor. The user is in the supine position, with the tools or probes positioned on muscles on either side of the upper back. In FIG. 32, the user is in a semi-reclined position, with the probes or tools positioned under the piriformis muscle in the buttock.

The user, optionally with the help of a therapist, selects the tool tip size (usually commencing with a largest size), stack height and angle to best apply pressure to the trigger point. The user places the tool (or stacked components) on a flat, firm, stable surface. The user or the therapist locates the first trigger point to be treated. The user lies on the tool bringing the probe in contact with the trigger point. The user then allows body weight to settle onto the point, while concentrating on relaxation and the sensation of the trigger point being treated. A feeling of decreased pain and/or tension in the area of the trigger point indicates successful "release" of the trigger point and the user can then seek out another trigger point in the same area. This process can be repeated several times in the same area, though not on the same trigger point. The user may need to adjust the probe size, stack height and probe angle, or add probes as desired depending on the success of the original choice of probe, and comfort level.

A recommended, though not limiting, sequence of decisions regarding probe size and height for first time users is as follows:

1. Select the largest-tipped probe and use the probe alone (no stacking).

2. Bring the probe into contact with the trigger point.

3. Stack the probe on one disk and then another as needed, based on the desire to penetrate deeper into the muscular and/or tendinous tissue, and within reasonable comfort levels. Utilize the wedge components in a stack as desired.

4. Utilize more than one tool to treat more than one trigger point simultaneously as desired. For example, the paraspinal muscles on each side of the spine, or at the occiput (muscular attachments at the base of the skull). Angled probe orientations for the vertical would be preferable in this instance. The probes may be rotated on the wedge bases, or on another sloped disk, to change the angle of the force application.

5. Select a smaller-tipped probe as dictated by the need to penetrate deeper into the muscular and/or tendinous tissue to effect suitable trigger point pressure within reasonable comfort levels. Larger probes should be used for trigger points that are more superficial, tender, or where there is less adipose tissue to penetrate. They should also be used where significant body weight may engage the probe, such as the back or buttocks. Smaller-tipped probes are preferably used for smaller muscle groups and/or lighter pressure, such as the hands or feet.

Additional features can be provided to the system that enhances its therapeutic effects. For example, a vibrating element can be disposed inside of the tool, or a vibrating tool can be provided. Similarly a heating or a cooling element can be provided to the tool, or the tool can be heated or cooled. The tips of the probes may also be configured to deliver various waveforms of direct current (DC) therapeutic electric stimulation to the user.

An optional strap attachment allows users to reach and treat trigger points in additional relaxed ways. Also, the strap can be used to generate leverage using the power muscles of the leg and torso to increase the force exerted on certain trigger points. Such use is not reliant on the strength of the user and enables the user to focus on relaxed breathing. The strap attachment comprises a length of flexible strap with an attachment feature that is configured to secure the tool to the strap.

Figure 36:
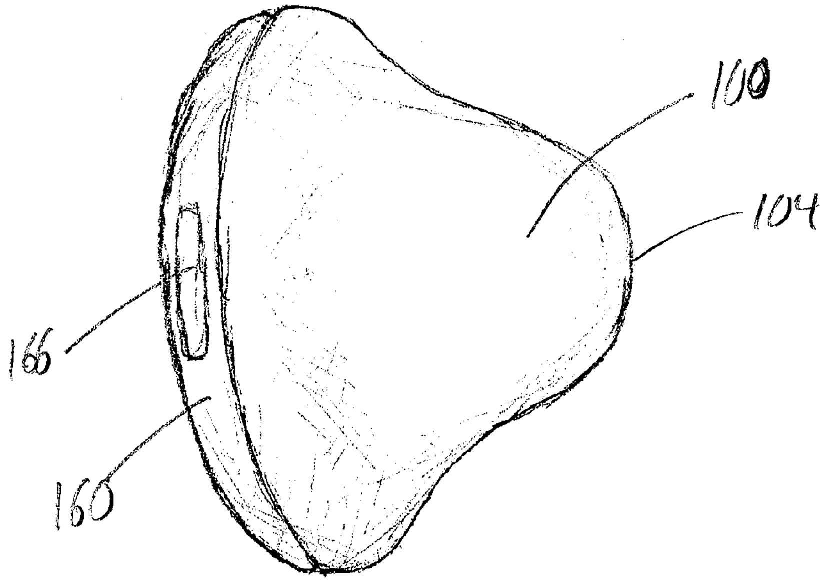
FIG. 36 is a perspective view of a strap attachment ring combined with a therapy tool according to certain embodiments.
Figure 37:
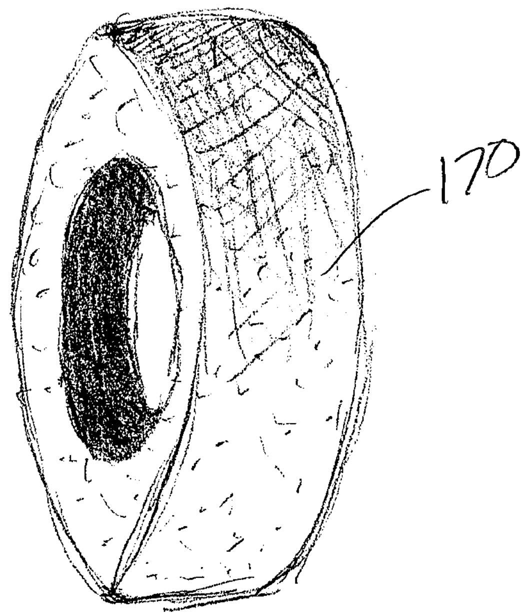
FIG. 37 is a perspective view of a cushion for a strap attachment ring according to certain embodiments.

Referring to FIGS. 33-37, a generally disk-shaped, donut-shaped or ring-shaped strap attachment can be used to secure the therapy tool to a strap. The attachment ring 160 comprises a dished receiving inside surface 162 and an outer surface 163. An upwardly extending portion of the outer surface forms a sidewall 164. Opposing parts of the sidewall include slots 166 through which the strap 168 can be threaded. This allows adjustability of the placement of the tool for the user and also allows the tool to be worn like a belt. The strap can also be used looped around the knee or foot of the user, seated in cross-legged or long-sitting positions respectively to enable pressure application without relying on upper extremity strength, and simultaneously affording relaxation of the user. FIG. 36 illustrates the tool 100 attached to the ring 160 with the tip 104 of the tool extending upwards from the inside surface. Alternatively, a cushion 170, shown in FIG. 37, can be placed against the inside surface of the ring and the tip of the tool can be inserted through a hole or aperture 172 in the ring so that the tip protrudes outwardly from the bottom surface.

Figure 38:
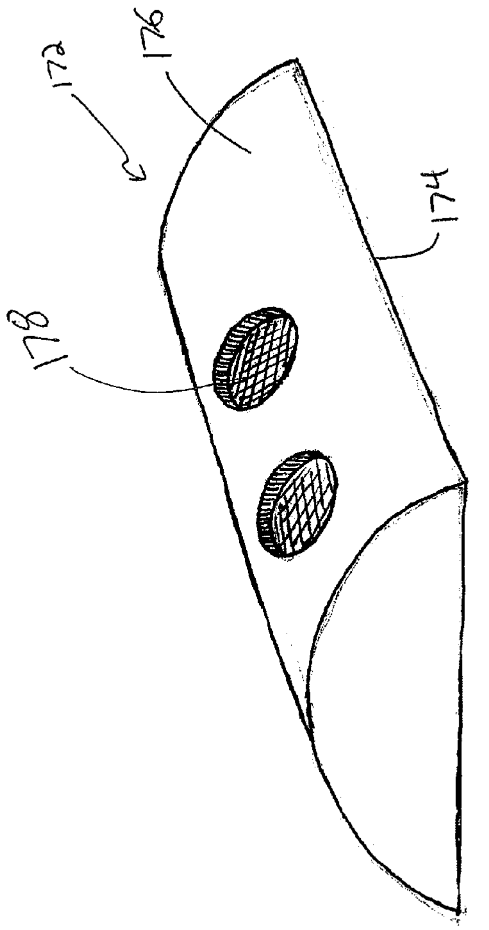
FIG. 38 is a perspective view of roller attachment component according to certain embodiments.

Referring to FIG. 38, a roller component 172 is shown. The roller attachment 172 comprises a curved outer surface 174 and a generally flat base 176. The base can also be curved. One or more apertures 178 are defined in the curved outer surface and configured to receive the base of one or more neuromuscular release therapy tools, including those disclosed in this specification. For example, the base 106 of tool 100 shown in FIGS. 1-15 can be securely placed in the aperture 178. Then the user can roll the target body part over the tool. In one alternative configuration, the apertures can be configured as one or more slots to provide the use with additional adjustability. More than one longitudinal row of apertures or slots can also be provided.

There are many features and advantages of certain embodiments of the trigger point therapy system 150. The system combines the reach and leverage of shepherd's crook-based devices with the simplicity of a hand-held device. The system does not rely for efficacy on a user's strength, reach, agility or flexibility. The system can be used without a partner; it is designed to be lain, leant, sat on, or used with a strap or roller attachment. The system is compact, discrete, lightweight and multi-purpose. The system allows users to apply acute, accurate and finely calibrated pressure to soft-tissue without making extreme demands on their strength, endurance, agility or stamina. The pressure applied to soft tissue can be increased without losing acuity. This is in contrast to balls and rollers: using a larger ball or roller to increase pressure results in a loss of acuity due to the increased radius of the ball or roller. The bell curve shape allows the tip or point of the probe to be placed in close proximity to bone. By contrast balls and rollers are convex, making it impossible to reach some areas of soft tissue with these other devices.

In certain embodiments, the system has three degrees of freedom: the force, acuity and angle of inclination of the pressure applied to the soft tissue can all be varied independent of one another. Force is configured via the nesting facility, the stacking disks, the rocker bottom and the strap and roller attachments. Force can be increased or reduced without a change in effort on the part of the user, unlike conventional trigger-point therapy devices. The acuity of the pressure can be varied by selecting different tip sized probes. Acuity thus can be adjusted without affecting force or inclination. The angle of inclination between the probe and the soft tissue can be varied by rotating two stacker wedge disks relative to one another, or by using the rocker bottom. Thus inclination can be varied without affecting force or acuity.

The tool and components can be leant, lain, or sat on or used with a strap or roller attachment to allow users to relax and concentrate on their breathing, two key ingredients to successful neuromuscular release, rather than focus on applying pressure to the tool. This is in contrast with many other tools, such as balls and rollers, for example, which require a degree of physical strength on the part of the user.

The accuracy with which force can be applied and the high degree of user control allows users to confidently treat soft tissue that they might feel uncomfortable treating with a less subtle tool or the intervention of a therapist, for example the pelvic floor muscles.

The modular system facilitates the incremental addition of features and components without necessitating the user to replace their existing system.

The system permits the user to vary pressure (force per unit area) to soft tissue. "Force" can be adjusted by varying position (lying down, sitting, standing) and height, and "unit area" could be adjusted by selecting different sizes of probe (or probe tip sizes).

The system can also be used to apply pressure to length and tension sensors buried within muscles and tendons known as muscle spindles and Golgi tendon organs respectively. These neuromuscular structures continuously relay information to the spinal cord to effect changes in muscle activation, thereby impacting muscular performance in terms of speed, power and length of muscle.

The system only requires a minimal set-up time. It is easy to keep clean. It is intuitive and easy to use. Moreover, the system is robust. For example, conical and bell-shaped probes or tools are inherently strong and demonstrate a high degree of stability when lain, sat or leant on.

The various components can be formed using conventional materials and manufacturing methods. For example, various plastics, rubber, rubberized metal, ceramics, composites or other suitable materials that resist deformation can be employed. The components can be formed, for example, using conventional processes, such as injection molding. Those skilled in the art will recognize that other materials and processes can be employed without departing from the scope of the invention.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A neuromuscular release therapy system comprising:

a plurality of tools, each of the plurality of tools comprising a body, the body being one single piece and including an outer surface, an inner surface, a rounded and solid tip defined at an upper-most portion of the body, a base, a stop surface defined in the body outer surface, a pocket defined by the inner surface and extending from the base upwards in the direction of the tip, and a recessed groove defined in the inner surface and extending upwards from the base and having a groove diameter and depth, wherein the body is generally bell-shaped with the base having a larger diameter than the tip;

a rocker base, the rocker base comprising a solid and continuous curved bottom surface, an upper surface and a flange extending upwardly from the upper surface, the flange having an outer diameter smaller than the diameter of the groove and a height smaller than the depth of the recessed groove; and a plurality of risers, each of the risers including a recessed groove extending upwardly from a bottom surface thereof and a flange extending upwardly from an upper surface thereof, wherein each of the plurality of tools can stack on the rocker base and on each of the plurality of risers, and wherein each of the plurality of tools are configured to stack on top of each other.

2. The system of claim 1, wherein the riser upper surface is generally parallel to the riser bottom surface.

3. The system of claim 1, wherein a plane of the riser upper surface intersects a plane of the bottom surface in an acute angle.

4. The system of claim 1, wherein a riser outer surface spanning between the upper and lower surfaces includes a rotational alignment indicator disposed thereon.

5. The system of claim 1, wherein the riser further includes a flange extending upwardly from the upper surface thereof.

6. The system of claim 1, wherein the riser further includes a raised surface extending upwardly from the upper surface thereof.

7. The system of claim 1, wherein the riser further includes a downwardly facing recess defined into the bottom surface thereof.

8. The system of claim 1, wherein the outer surface of the riser spanning between the upper and lower surfaces is circumferential and vertically oriented.

9. A neuromuscular release therapy kit comprising:

a plurality of therapy tools, each comprising a base, a rounded and solid tip and an outer surface spanning between the base and tip, the therapy tool being a one single piece component;

a plurality of risers, each comprising an upper surface, a bottom surface and a sidewall extending between the upper surface and the bottom surface; and a rocker base comprising a rounded bottom surface and a top surface, wherein the base of the therapy tool is configured to stack on both of the upper surface of the riser and the top surface of the rocker base, wherein each of the tools, each of the risers and the rocker base include respective flanges and recesses configured so that each of the tools can stack on the rocker base and on each of the risers, and the riser can stack on the rocker base, wherein the each of the tools are configured to nest inside of adjacent tools, each tool having a similar configuration.

10. The kit of claim 9, wherein each of the risers is a wedge in a side profile view.

11. The kit of claim 9, wherein each of the therapy tools comprises a different tool tip diameter.

* * * * *